US009248146B2

(12) United States Patent
Barnhart et al.

(10) Patent No.: US 9,248,146 B2
(45) Date of Patent: *Feb. 2, 2016

(54) DISSOLVABLE ADHESIVE FILMS FOR DELIVERY OF PHARMACEUTICAL OR COSMETIC AGENTS

(75) Inventors: Scott D. Barnhart, York, PA (US); Andrew P. Full, York, PA (US); Cathy M. Moritz, Red Lion, PA (US); William G. Meathrel, York, PA (US); George Cramer, York, PA (US); Mary Robertson, Castletroy (IE)

(73) Assignee: Adhesives Research, Inc., Glen Rock, PA (US)

( * ) Notice: Subject to any disclaimer, the term of this patent is extended or adjusted under 35 U.S.C. 154(b) by 1133 days.

This patent is subject to a terminal disclaimer.

(21) Appl. No.: 11/907,372

(22) Filed: Oct. 11, 2007

(65) Prior Publication Data

US 2008/0124381 A1 May 29, 2008

Related U.S. Application Data

(63) Continuation-in-part of application No. 10/970,391, filed on Oct. 22, 2004, now abandoned.

(60) Provisional application No. 60/513,547, filed on Oct. 24, 2003.

(51) Int. Cl.
| | |
|---|---|
| *A61F 13/00* | (2006.01) |
| *A61K 31/717* | (2006.01) |
| *A61K 8/02* | (2006.01) |
| *A61K 8/73* | (2006.01) |
| *A61K 9/00* | (2006.01) |
| *A61K 9/70* | (2006.01) |
| *A61K 31/716* | (2006.01) |
| *A61L 15/28* | (2006.01) |
| *A61L 15/44* | (2006.01) |
| *A61L 15/64* | (2006.01) |
| *A61Q 19/00* | (2006.01) |

(52) U.S. Cl.
CPC .............. *A61K 31/717* (2013.01); *A61K 8/0208* (2013.01); *A61K 8/731* (2013.01); *A61K 9/0014* (2013.01); *A61K 9/0056* (2013.01); *A61K 9/7007* (2013.01); *A61K 31/716* (2013.01); *A61L 15/28* (2013.01); *A61L 15/44* (2013.01); *A61L 15/64* (2013.01); *A61Q 19/00* (2013.01); *A61F 2013/0071* (2013.01); *A61F 2013/0091* (2013.01); *A61F 2013/00646* (2013.01); *A61F 2013/00685* (2013.01); *A61F 2013/00719* (2013.01); *A61F 2013/00906* (2013.01); *A61F 2013/00914* (2013.01); *A61L 2300/254* (2013.01); *A61L 2300/402* (2013.01); *A61L 2300/404* (2013.01); *A61L 2300/412* (2013.01); *A61L 2300/418* (2013.01); *A61L 2300/604* (2013.01)

(58) Field of Classification Search
USPC .......................................................... 424/49
See application file for complete search history.

(56) References Cited

U.S. PATENT DOCUMENTS

| | | | |
|---|---|---|---|
| 3,983,209 A * | 9/1976 | Schmitt .......................... 424/444 |
| 5,049,395 A * | 9/1991 | Chang ............................ 424/494 |
| 5,254,338 A | 10/1993 | Sakai et al. |
| 5,393,528 A * | 2/1995 | Staab ............................. 424/436 |
| 6,923,981 B2 * | 8/2005 | Leung et al. .................. 424/439 |
| 7,067,116 B1 * | 6/2006 | Bess et al. ..................... 424/78.1 |
| 2003/0068376 A1 * | 4/2003 | Chen et al. ..................... 424/484 |
| 2004/0018156 A1 * | 1/2004 | Szeles et al. .................... 424/50 |
| 2007/0082041 A1 | 4/2007 | Walters et al. |

FOREIGN PATENT DOCUMENTS

| | | |
|---|---|---|
| JP | 2002-535269 T | 10/2002 |
| JP | 2006-515333 | 5/2006 |
| WO | WO-00/42992 A2 | 7/2000 |
| WO | WO 01/70194 A | 9/2001 |
| WO | WO-03/030881 A1 | 4/2003 |
| WO | WO-2005-039499 * | 5/2005 |
| WO | WO 2005/039499 A2 | 5/2005 |

OTHER PUBLICATIONS

Supplementary European Search Report dated Dec. 3, 2007.

* cited by examiner

*Primary Examiner* — Frederick Krass
*Assistant Examiner* — Celeste A Roney
(74) *Attorney, Agent, or Firm* — McNees Wallace & Nurick LLC

(57) ABSTRACT

The invention provides disintegratable adhesive films containing a mixture of high molecular weight and low molecular weight water soluble components; and a pharmaceutically or cosmetically active ingredient. Optionally, the films contain a starch component, a polysaccharide component, a filler, a plasticizer and/or humectant. The films are preferably in the form of an adhesive layer having a thickness sufficient to disintegrate, when exposed to a moist environment and/or a trigger compound, and release the active ingredient. The films can be cut to any desired size or shape to provide conveniently useable unit dosage forms for administration to wet or moist body surfaces for human, pharmaceutical, cosmetic, or veterinary applications. The invention further provides various end uses and methods of administering the film compositions.

10 Claims, No Drawings

DISSOLVABLE ADHESIVE FILMS FOR DELIVERY OF PHARMACEUTICAL OR COSMETIC AGENTS

CROSS REFERENCE TO OTHER APPLICATION

This patent application is a continuation-in-part application of U.S. application Ser. No. 10/970,391, filed on Oct. 22, 2004 now abandoned, and titled RAPIDLY DISSOLVING FILMS FOR DELIVERY OF PHARMACEUTICAL OR COSMETIC AGENTS, which in turn claims the benefit of U.S. provisional patent application Ser. No. 60/513,547, filed Oct. 24, 2003, the entire disclosures of which are incorporated herein by reference in their entirety.

FIELD OF THE INVENTION

The present invention is directed to dissolvable adhesive films and methods for delivering pharmaceutically active or cosmetic agents to animals and humans in need thereof. The present invention provides in one embodiment a water soluble adhesive film composition containing an active pharmaceutical ingredient for topical administration in unit dosage form. The adhesive film composition, when exposed to moisture or a trigger compound, disintegrates to release the active pharmaceutical ingredient contained therein.

BACKGROUND OF THE INVENTION

Disintegratable films can provide a convenient and effective delivery vehicle for delivering active ingredients, such as pharmaceutical compounds, to a moist body surface of humans and animals. When exposed to moisture, for example, upon placement in the oral cavity, the film disintegrates and releases the active ingredient. However, the film should have adequate strength for processing and use as a unit dosage form, and also ensure appropriate release of the active ingredient while eliminating or minimizing any undue discomfort to the applied area.

U.S. Pat. Nos. 4,029,757; 4,029,758; and 4,031,200 refer to pharmaceutical dosage units formed from a multiplicity of edible webs that are sealed. One layer is fabricated by "fan folding" and compressing a continuous web structure, and subsequently sealing the composite into a geometric shape. The films rely on a complex process of fan folding and sealing to maintain the pharmaceutical compound internally within the multilayered dosage form.

U.S. Re 33,093 refers to controlled-release medicament-containing single or multi-layer thin films for intra-oral drug delivery. The thin film includes a polymeric matrix layer of 20-93% by weight of a hydroxypropyl cellulose having a molecular weight above 100,000; 5-60% of a homopolymer of ethylene oxide having a molecular weight from 3,000,000-5,000,000; 0-10% of a water insoluble polymer selected from the group consisting of ethyl cellulose, propyl cellulose, polyethylene and polypropylene; 2-10% of a plasticizer; and a pharmaceutically effective amount of medicament. The controlled-release films of U.S. Re. 33,093 are relatively slow to dissolve/disintegrate in the mouth.

U.S. Pat. No. 5,984,430 (Reexamination Certificate issued Mar. 4, 2003); U.S Pat. Nos. 6,177,096; and 6,284,264 refer to oral films for the delivery of pharmaceutical and cosmetic compounds. The compositions referred to in these patents contain a water-soluble polymer, a polyalcohol, a surfactant, and a pharmaceutically or cosmetically active ingredient. According to these patents, inclusion of the surfactant component imparts "instant wettability" followed by rapid disintegration of the film when placed into an aqueous environment such as the oral cavity.

U.S. Pat. No. 4,136,145 refers to a pharmaceutical unit dosage composition in which the pharmaceutically active medicament is uniformly dissolved or suspended in a flexible, water-soluble film carrier. The compositions include various drug compounds, water-soluble polymers, surfactants, release agents, parting compounds, and fillers.

U.S. Pat. Nos. 5,393,528 and 5,529,782 refer to dissolvable films for contraception or for the internal or topical delivery of a medication. According to these patents, the dissolvable films require the use of an inert gas to entrap bubbles in the polymer matrix to create a foamed film. The foam structure is required to control the dissolution rate and also to provide a perception of softness to the film.

Each film delivery system can be characterized by its film strength and its disintegration profile (the speed at which the film will disintegrate in an aqueous media, such as water, saliva and other bodily fluids, and/or in the presence of a trigger compound). Surfactants have been used to affect the disintegration speed and decrease the time required for complete film disintegration and thus release of the active ingredient. The present invention provides disintegratable film compositions that disintegrate upon exposure to moisture and/or a trigger compound, and which, at the same time, have sufficient film strength without requiring the use of any surfactant. While a surfactant is optional in certain embodiments of the present invention, as described below, other embodiments are surfactant-free or substantially free of surfactants.

BRIEF SUMMARY OF THE INVENTION

The present invention provides disintegratable adhesive film compositions prepared with a combination of ingredients that yield films of sufficient film strength and variable disintegration profiles. Films prepared pursuant to this invention yield similar or improved disintegration speeds as compared to prior art films, including the prior art surfactant-containing films.

The films according to the present invention contain a mixture of high molecular weight and low molecular weight water soluble components; and a pharmaceutically or cosmetically active ingredient. Optionally, the films further contain a starch component, a polysaccharide component, a plasticizer and/or a humectant. Also optionally, the films can include a filler, which is a dispersed phase or particle within the film and which, in certain embodiments, can cause faster disintegration of the films.

The films are in the form of a monolayer or a multilayer having a thickness sufficient to disintegrate in a wet or moist environment and/or in the presence of a trigger compound, and can be applied or removed with minimum or no trauma to the applied area. The films can be cut to any desired size or shape to provide conveniently useable unit dosage forms for human, pharmaceutical, cosmetic, or veterinary applications. The films are preferably adhesive, in that upon exposure to moisture the films adhere to the applied area until disintegration.

The invention further provides methods of administering the adhesive film compositions by placing the film, for example, into the oral cavity, a surgical area, or topically to skin injuries or conditions such as burns, rashes, irritations, ulcers, and wounds for a sufficient period of time to permit the film to disintegrate and release the active ingredient.

These and other advantages and features of the invention will be more readily understood from the following detailed description.

DETAILED DESCRIPTION OF THE INVENTION

Reference will now be made in detail to the presently preferred embodiments of the invention, which, together with the following examples, serve to explain the principles of the invention. These embodiments are described in sufficient detail to enable those skilled in the art to practice the invention, and it is to be understood that other embodiments may be utilized, and that various structural, biological, and chemical changes may be made without departing from the spirit and scope of the present invention.

The present invention provides compositions and methods for the use of adhesive film compositions which can be processed into single layer (monolayer) unit dosage forms or combined with other layers to prepare multilayer dosage forms comprising a film as described herein containing a pharmaceutically active or cosmetic ingredient. The disintegratable adhesive films according to the invention contain a mixture of high molecular weight and low molecular weight water soluble components; a pharmaceutically or cosmetically active ingredient; optionally a starch component, a polysaccharide component, a plasticizer and/or humectant; and/or other excipients in suitable amounts as described below, or which may be determined by one of ordinary skill in the art pursuant to the guidance provided by the examples and teachings herein. The films will typically have a thickness in the range of about 10 to about 200 microns, although various other thicknesses are suitable as desired for particular applications as described in more detail below.

The term "surface" as in "body surface" is intended to include external (topical) and internal body surfaces, such as skin, nails, and mucosal tissue (e.g., sublingual, buccal vaginal, rectal, urethral), as well as surfaces in and around the oral cavity (e.g., teeth, lips, gums, mucous membranes), and surfaces of wounds and also other internal surfaces which may be exposed by trauma or surgery.

According to one embodiment, the disintegratable adhesive films according to the invention achieve their desirable characteristics of film strength and disintegration profile while requiring no and containing no or substantially no surfactants, release agents, or parting compounds, such as those found in U.S. Pat. Nos. 4,136,145 and 5,984,430. The term "essentially free of surfactants" refers to trace amounts or higher levels of surfactants that are sufficiently low so as not to substantially increase the disintegration rate of the film composition following contact with a wet or moist body surface, or following application of moisture to a dry body surface.

According to another embodiment, the disintegratable adhesive films according to the invention contain a filler. The filler is a dispersed phase or particle that in preferred embodiments causes the films to disintegrate faster upon contact with the targeted body surface than without the filler. The filler can be an optional component. Alternatively, in other embodiments, the active ingredient, when present in the film as a dispersed phase or particle, can serve the same purpose as a filler.

In one exemplary embodiment, the water soluble components of the films according to the present invention include any pharmaceutically acceptable or food grade water-soluble polymers, including but not limited to, water-soluble hydroxypropylmethyl cellulose, hydroxyethyl cellulose, hydroxypropyl cellulose, polyvinyl pyrrolidone, carboxymethyl cellulose, sodium carboxy methyl cellulose, methyl cellulose, polyvinyl alcohol, sodium alginate, polyethylene glycol, xanthan gum, tragacantha, guar gum, acacia gum, arabic gum, carrageenan, polyacrylic acid, methyl[meth]acrylate copolymers, carboxyvinyl copolymers, and various mixtures of the above and other known water-soluble polymers, cellulose derivatives, and/or gums.

We have found that particularly beneficial properties are obtained when the water soluble polymeric component includes a combination of low molecular weight polymers (e.g., those less than about 5,000 to about 60,000 daltons) and high molecular weight polymers (e.g., those of about 60,000 to about 150,000 daltons, and to about 500,000 daltons or higher). For example, a combination of hydroxypropyl cellulose (e.g., KLUCEL®, grade JF, Hercules Inc., Aqualon Division) and hydroxypropyl methylcellulose (e.g., Methocel, grades E5, E50, E4M, and SG A16M by Dow Chemical) is suitable. These water soluble cellulose derivative polymers have molecular weights of about 140,000; 30,000; 90,000; 400,000; and greater than about 100,000 daltons, respectively.

Additional water soluble polymers include polyvinyl pyrrolidone (PVP), such as Plasdone K-29/32 by ISP Corp., which has a molecular weight of about 58,000 daltons; a polyvinyl alcohol-polyethylene glycol copolymer, such as Kollicoat IR by BASF Pharma, which has about 75% polyvinyl alcohol units and 25% polyethylene glycol units and has a molecular weight of about 49,000 daltons; butylated PVP, such as Ganex P-904 LC by ISP Corp., which has a molecular weight of about 16,000 daltons; and Gantrez S copolymers, such as Gantrez S-97 by ISP Corp., which has a molecular weight of about 1,500,000 daltons. Further, a water soluble polymer may serve the function of an additional optional component. For example, polyethylene oxide, specifically Polyox by Dow, having a molecular weight of about 200,000 daltons, can serve as a high molecular weight water soluble polymer and a plasticizer, as discussed below.

The molecular weights of the water soluble polymers can be determined as described in Keary, "Characterization of METHOCEL Cellulose Ethers by Aqueous SEC with Multiple Detectors," Carbohydrate Polymers Vol. 45, pp. 293-303 (2001), which is incorporated herein by reference.

Various other polymers can be selected by one of ordinary skill in the art given the teachings herein, so long as the polymer is water soluble, and preferably includes a sufficient amount of a high molecular weight component to impart adequate film strength, and a sufficient amount of a low molecular weight component to facilitate the desired film property of rapid disintegration profile. Various concentrations of each polymer may be utilized. Such concentrations will typically be in the range of about 0.5% to about 99% for each polymer based on the total weight of the dry film. In one embodiment, the concentration for the high molecular weight polymer is about 5% to 10% and the concentration of the low molecular weight polymer is about 5% to 10% of the dry film.

According to another exemplary embodiment of the invention, the water soluble low molecular weight component need not be a water soluble polymer. Instead, the low molecular weight component may be a low molecular weight monomer or a combination of various low molecular weight monomers. The low molecular weight component can also serve the function of an additional optional component. For example, the low molecular weight component can also serve as the active ingredient, a polysaccharide component, a plasticizer, starch, flavoring, colorant, and/or sweetener, and may include any of the specific compounds listed below or other suitable compounds, which are water soluble and have a molecular weight less than about 60,000 daltons. The low molecular weight component serves to promote rapid disintegration, but is present in an amount such that film strength is adequate for processing and dispensing. Various concentrations of the low molecular weight component can be utilized. Such concentrations will typically be in the range of about 0.5% to about 99% or more based on the total weight of the dry film. In one embodiment, the concentration for the high molecular weight polymer is about 5% to 10% and the concentration of the low molecular weight component is about 30% to 80% of the dry film.

Any pharmaceutically or cosmetically active ingredient may be used in accordance with the principles of this invention, whether dissolved or dispersed. Examples of pharmaceutically active compounds include hormones, e.g., cyproterone acetate, progesterone, estradiol, testosterone, insulin, triiodthyronin, cortisone, etc.; prostaglandins, e.g., prostaglandin $E_1$, prostaglandin $E_2$, prostaglandin $A_1$ and prostaglandin $F_{2\alpha}$; vitamins, e.g., vitamin A, vitamin $D_2$, vitamin $D_3$, vitamin E, vitamin $K_1$, vitamin $K_2$ and derivatives of vitamin $B_1$, e.g., thiamine tetrahydrofurfuryl disulfide or thiamine propyldisulfide; antibiotics, e.g., erythromycin and tetracycline; contraceptives, e.g., chlormadinone, chlormadinone acetate, megestrol acetate, d-norgestrel, medroxyprogesterone acetate, norethisterone, norethisterone acetate, etc.; spermicides, e.g., p-diisobutylphenoxypolyethoxyethanol, gestagens, estrogens and mixtures thereof; anxiolytics, sedatives, and hypnotics, such as bezodiazepines, e.g., diazepam and alprazolam, buspirone HCL, promethazine HCL, phenobarbital; cerebral stimulants, such as methylphenidate HCL, pemoline, caffeine; anti-diabetics; sulfonamides; proton pump inhibitors, such as omeprazole; trichomonal agents; anesthetics/analgesics, such as benzocaine, lidocaine, procaine, dyclonine HCl, phenol, aspirin, phenacetin, acetaminophen, potassium nitrate, etc.; opiate agonists, such as fentanyl citrate, meperidine HCL, morphine sulphate; anticaries agents, such as sodium fluoride, sodium monofluorophosphate, stannous fluoride, etc.; anti-inflammatories, such as hydrocortisone acetate, triamcinolone acetonide, dipotassium, glycyrrhizinate, etc.; antihistamines, such as chlorpheniramine maleate, ephedrine HCl, diphenhydramine HCl, clemastine fumarate, loratadine, cetirizine, etc.; decongestants, such as pseudoephedrine; antibacterials, such as chlorhexidine, cetylpyridinium chloride, benzethonium chloride, dequalinium chloride, silver sulfadiazene, other silver salts, phenol, thymol, hexedine, hexetidine, alexidine, etc.; fungistats, such as nystatin, miconazole, ketoconazole, etc; antitussives, such as dextromethorphan, codine sulphate, menthol, etc.; anti-diarrheal agents, such as loperamide; antianginals, such as nitroglycerin, isosorbide mononitrate, isosorbide dinitrate, and other nitric oxide derivatives; antiemetics, such as meclazine HCL; anti-flatulents, such as simethicone; miscellaneous autonomic and central nervous system agents, such as nicotine and sumatriptan, respectively; skeletal muscle relaxants, such as baclofen; antidepressants generally, such as olanzapine, risperidone, and specifically monoamine oxidase (MAO) inhibitors, e.g., phenelzine, selegiline, tricyclic antidepressants, e.g., amitriptyline HCL, clomipramine HCL, imipramine HCL; antipsychotics, such as phenothiazine derivatives, butyrophenone derivatives, e.g., haloperidol; smoking deterrents, such as bupropion; alcohol deterrents, such as disulfiram, naltrexone; enzymes, such as papain; cosmetic active ingredients, such as parsley seed oil; among others.

The optional polysaccharide component of disintegratable adhesive films according to the invention can be added as a sweetener and/or to promote rapid disintegration of the film. Preferably, the glucose component comprises a water soluble polymer or mixture of polymers having D-glucose units. The dextrose equivalent (DE) of the glucose component is preferably within the range of about 10 to about 25, or about 15 to about 20, although various other DE ranges can also be used. The glucose component can be prepared, for example, by the partial hydrolysis of starch to yield D-glucose polymer mixtures. Suitable commercially available glucose components include, for example, maltodextrin, corn syrup solids, sucrose, and dextrose. Maltodextrin having a DE of about 16.5 to 19.5, such as that commercially available from Grain Processing Corp. (GPC) under the trade name "Maltrin M180," is particularly suitable, although various other glucose containing polymers and mixtures can be utilized, including, for example, other grades of "Maltrin," "Lycatab DH" (Roquette Freres), and "Star-Dri" (A. E. Staley). Suitable concentrations as a weight percentage of the dry film composition will typically be in the range of about 0.5% to 99%, or about 3% to about 15%, although other concentrations also may be used depending on the selection of other components and the desired film properties.

The optional starch component of disintegratable adhesive films according to the present invention can be added to promote rapid disintegration of the film and/or to aid in film formation. Preferably, the starch component is a water soluble polysaccharide composition containing amylose and/or amylopectin. Such compositions may be prepared by, for example, modifying natural starches, such as corn, wheat, rice, potato, or tapioca starch, to provide cold water soluble instant starches. Various water soluble compositions of amylose and/or amylopectin polysaccharides can be used. Typically, these can be made by heating a natural starch with steam to modify the natural starch product so that it is cold water soluble.

The instant starch commercially available from GPC, Muscatine IA, as "Instant Pure Cote B792," (IPC B792) is an exemplary starch component for purposes of the present invention. Other suitable commercially available instant starches include "Polartex Instant 12640," available from Cargill, Inc., and various others may also be utilized. The starch component will typically have an amylose to amylopectin ratio in the range, for example, of about 0 to about 2.5. The optional starch can be incorporated in the wet film composition in any suitable amount, including, but not limited to, about 0.5% to 50%, or about 3% to about 35% by weight based on the dry film.

The disintegratable adhesive film compositions of the present invention may also optionally contain a plasticizer or humectant, for example, polyalcohols, sorbitan esters, and citric acid esters, to increase the flexibility of the films. The plasticizers can be added directly to the formulation during manufacture. Suitable compounds include polyethylene glycol (PEG), such as Lutrol E 400, by BASF Pharma; polyethylene oxide, such as Polyox by Dow; polyoxamers, such as Lutrol F by BASF Pharma; polyvinyl alcohol; polyvinyl methyl ether, such as Lutanol by BASF; or mixtures of those polymers; triacetin; glycerin; mannitol; xylitol; and various other polyalcohols and other compounds having plasticizer and/or humectant properties can be satisfactorily employed. Sorbitol and PEG 400 are particularly suitable; although compounds having a higher molecular weight (e.g., Polyox N80) than PEG 400 may be desirable for certain applications, since they are typically less volatile than sorbitol and PEG 400. The optional plasticizer and/or humectant may be present in any suitable range, including, for example about 0.5% to 30%, 10% to 20%, or 15% to 18% by weight of the dry film.

Additional optional components can be added to films according to the invention. For example, flavors and sweeteners can be added to the film formulations of this invention to make the film more palatable to the patient or consumer for oral delivery. Flavors and sweeteners can be added directly to the formulation during manufacture. Flavors, sweeteners, artificial and natural, are known to those skilled in the art. The choice of flavor, sweetener, and/or other optional ingredients is not important for the practice of this invention.

Also, any color can be imparted to the film, depending upon the dye or pigment that is used. For oral applications, the dye or pigment is typically an FD&C colorant that is approved for oral consumption. Further, buffers, stabilizers, additives and/or other components can be added to film formulations according to the invention to provide a film having desired properties.

As noted above, according to one embodiment, the films according to the invention also contain a filler. The filler is a dispersed phase or particle that, in preferred embodiments, causes the films to disintegrate faster upon contact with the targeted wet or moist body surface or upon application of moisture after the film is applied to a dry body surface. The active ingredient can itself act as a filler in certain embodiments. The term "moist" herein, shall be understood to mean applying, including, or containing on the applicable surface at least a sufficient amount of aqueous material to cause dissolution and disintegration of the film within a desired time. For example, a taste masked drug (e.g., encapsulated dextromethorphan or diphenhydramine) can act as a filler and promote rapid disintegration of the film. The encapsulated or taste masked drug is a dispersed particle. Methods of taste masking include encapsulation or complexation. For example, MicroMask® pseudoephedrine by Particle Dynamics is an encapsulated form of psuedoephedrine. Additionally, when the active ingredient is present in the film at a concentration above its solubility saturation point, the excess active ingredient can act as a filler. For example, when caffeine is the active ingredient, the film can be supersaturated with the caffeine such that the excess caffeine acts as a disintegration-promoting filler.

The filler can be an optional non-active component. Examples of such components include titanium oxide and microcrystalline cellulose, which is available under the name Avicel, among others. Air or other gasses can also be used as a filler according to the invention. When air is employed as the filler, a surfactant (e.g., sodium lauryl sulfate (SLS), available under the name Stepanol, Polysorbate 80, or Pluracare F87 Pril) may be included in the film formulation. The surfactant does not itself serve to significantly increase the rate of disintegration of the films upon contact with moisture. Instead, the surfactant aids in the processing and formation of the film. Specifically, the surfactant stabilizes the gaseous bubbles as a dispersed phase within a solution to allow the solution to be processed, as described in more detail below, to form the film containing the gas or air as a dispersed phase filler.

In a preferred embodiment, the films will self adhere to a wet or moist body surface without having to apply pressure to the film. As such, the film can be applied to a target area, for example, an open wound, burn, an irritated site, or other areas, with little or no additional trauma. Adhesive properties can be formulated into the film by, for example, incorporating biological adhesives such as natural gums (e.g., karaya gum and xanthan gum). Alternatively, addition of sugar, oligosaccharides, and polysaccharides can be used to provide skin adhesion properties. The films can easily be removed or washed off by contact with an aqueous fluid.

The film compositions according to the invention may be prepared by several methods, including, but not limited to, adding the combination of high and low molecular weight water soluble components, the optional starch, and optional glucose polymer ingredients to a solvent that is capable of dissolving them, such as water or ethanol or a mixture of ethanol and water. Upon forming a homogeneous solution, the active ingredient and any of the other optional components, such as plasticizers, flavors, sweeteners, colorants, and/or other components may be blended into the active-containing polymer solution. Alternatively, all of the film components may be added and concurrently blended to form a solution or dispersion. Also, a dry blend can be compounded by a V-blender. The dry blend can be subsequently used to form a solution or dispersion. Additionally, the dry blend can be subsequently subjected to a melt extrusion to form a film upon cooling. It should be understood that no particular sequence of steps is required, except as needed to effectively prepare a desired film composition. For example, when a particular sequence yields an undesirable precipitate, an alternative sequence is necessary.

The active ingredient may be soluble in the solution or it may be suspended or dispersed in the solution.

The active ingredient-containing solution or dispersion may be further processed into a film by any one of many casting, drawing, or extruding techniques. For example, the solution or dispersion may be sprayed onto a support such as a release-treated belt. Alternatively, for example, the solution or dispersion may be roll coated onto a release treated paper or film substrate.

After coating of the solution or dispersion onto a support surface, the solvent may be removed by radiant energy (such as infra-red), heat, convection, vacuum, or any combination of these to yield a dry film containing an active ingredient. The resulting dry film can be wound up into a roll for storage prior to further processing into unit dose forms. Whether stored for future processing or immediately following removal of the solvent, the resulting film can be removed from the support surface and subsequently processed into unit dose form. Additional ingredients can be applied to the dried film by, for example, printing, spraying, dusting, or vapor adsorption processes, among others.

The dry film can be processed into unit dose form by any suitable technique, including, for example, by die-cutting or cutting across the width of a singular narrow roll to prepare unit dosage forms of any desired geometric size or shape. The unit dose forms may be subsequently packaged with various suitable materials known in the art to prevent degradation and protect the active ingredient from adulteration.

According to one film embodiment, the films are adhesive monolayers having a thickness in the range of about 20 microns ($\mu$) to about 1200$\mu$, more preferably, less than about 250$\mu$, or equal to or less than about 200$\mu$. In another film embodiment, the films have a thickness of less than about 175$\mu$, or less than about 75$\mu$. When exposed to or placed on a wet or moist body surface, or upon application of moisture to trigger disintegration when the film is applied to a dry body surface, the films disintegrate or dissolve to release the active ingredient. By "disintegrate" or "dissolve", we mean that the active ingredient, or the taste masked, encapsulated, or complexed form of the active ingredient, is released from the film matrix in a matter of a few seconds to more than several hours or days. Disintegration times can be determined using the test provided by (USP) 24, Disintegration <701>. See United States Pharmacopoeia, 24th ed., Ch. 701, p. 1941 (2000), which is incorporated herein by reference.

Preferably, for oral delivery, the composition has already disintegrated in the oral cavity almost instantaneously or after less than several hours from initially placing the composition in the mouth. At the same time, the films have adequate strength for processing, packaging, and administration without physical failure (e.g., breakage, fracture, or otherwise) during processing and normal handling prior to administration to the intended wet or moist body surface. The film strength, specifically, film resilience, springiness and burst strength, can be determined using the TA.XT2i Texture Analyzer by Texture Technologies Corp. and the ASTM D3763 "High-Speed Puncture Properties of Plastics Using Load and Displacement Sensors" test method. These properties of film strength and disintegration profile are the result of the unique combination of the components described herein.

Alternatively, the films may disintegrate in the presence of a trigger compound. The trigger compound reacts with a component in the film, which initiates the film breakdown. Table 1 lists examples of trigger reagent-reactive component combinations.

TABLE 1

| Trigger Reagent | Reactive Component in Film |
| --- | --- |
| Cellulase | Cellulose and modified cellulose compounds |
| Amylase | Starch, polysaccharides |
| Glucose oxidase | Compounds with polysulfide groups |
| Metalloproteinase | Polypeptides |
| Collagenase | Peptide linkage |
| Alkaline phophatase | Phosphoester polyethylene glycol |
| Elastase | Proteins |
| Aqueous alkali | Polyester and polyurethane groups |

The film compositions may be administered to the oral mucosa or other mucous membranes where they are disintegrated by saliva and/or other aqueous materials on the mucosal surface. Upon disintegration, the films release one or more pharmaceutical or cosmetic compounds to the mucous membranes. The film compositions may be administered in such a manner so as to deliver an effective amount of the active ingredient, which may be present in pharmaceutically effective trace amounts up to about 60% or more of the dry film.

Moreover, the film compositions can be used to treat pressure sores, venous ulcers, and diabetic foot ulcers by administering, for example, enzymes, antimicrobials, topical analgesics, and/or agents such as activated carbon and activated alumina to reduce odor; to treat skin irritations and rashes such as diaper rashes by administering, for example, topical analgesics, antimicrobials, and/or pain relievers; and to treat burns by administering, for example, antimicrobials to help contain infections. The films can also be used to treat various other skin conditions such as psoriasis and open wounds.

The films of the present invention are preferably free standing films, but may be used in combination with bandages and gauze dressings. Upon administration, the films dissolve in water and/or biologically compatible aqueous fluids. In some applications, the films may exhibit different dissolution times or are dissolvable under different conditions, such as at higher or lower pH. In addition, other applications may utilize multilayered constructions combining dissolvable films with different active ingredients that are released in a controlled order and/or rate.

The following illustrative examples provide a number of specific formulations within the scope of the present invention. These examples are by way of illustration only and are not intended to be limiting in any way. Various alternative components, concentrations, and optional excipients (plasticizers, humectants, fillers, preservatives, etc.) may be utilized given the teachings herein to yield thin monolayer films of suitable film strength and disintegration profile.

The specific embodiments of examples 1-29 and 32-36 below contain no surfactants. Surprisingly beneficial film quality can thus be achieved without any surfactants. The embodiments of examples 11-31 each contain a dispersed phase filler. In examples 11-24, the active ingredient also serves as a filler; whereas, in examples 25-31 an additional component serves as a filler. The embodiments of examples 30 and 31 include air as the filler. Accordingly, examples 30 and 31 also include a surfactant for stabilizing the air bubbles during processing.

The exemplary formulations below are described in the following manner: 1) the concentrations of the excipients are expressed in parts in the dry film and/or the wet solution or dispersion; 2) the weight percent of the excipients in the dry film and/or the wet solution or dispersion; and/or 3) the amount of a stock solution (stock soln.) of the excipients expressed in grams, and the total weight of the wet solution or dispersion, and the total weight of the dry film expressed in grams.

EXAMPLES

Example 1

|  | Dry Film Concentration Parts |
| --- | --- |
| Methocel E5 | 10.0 |
| Methocel E50 FG | 8.0 |
| IPC B792 | 27.0 |
| Sucralose | 2 |
| Sorbitol | 5 |
| Sucrose | 10 |
| FD&C Red #40 | 0.15 |
| Cherry Flavor | 29.55 |
| Chlorpheniramine Maleate | 8.3 |
| Overall Sum | 100 |
| Solids | 20% |

Example 2

|  | Dry Film Concentration Parts | Wet % w/w |
| --- | --- | --- |
| Methocel E5 | 6.32 | 2.59 |
| Methocel E50 | 15.65 | 6.42 |
| Klucel JF | 2.67 | 1.10 |
| Maltodextrin M180 | 3.86 | 1.58 |
| IPC B792 | 3.71 | 1.52 |
| Citric Acid | 1.04 | 0.43 |
| Sucralose | 9.22 | 3.79 |
| Lemon-Grapefruit Flavor | 12.72 | 5.22 |
| Orange Flavor | 12.49 | 5.13 |
| Pseudoephedrine | 16.48 | 6.76 |
| Sorbitol | 13.78 | 5.66 |
| FD&C Red# 40 | 1.04 | 0.43 |
| FD&C Blue# 1 | 1.04 | 0.43 |
| Water | — | 58.95 |
| Overall Sum | 100.02 | 100.01 |
| Solids |  | 41.05% |

| | Example 3 | | Example 4 | |
|---|---|---|---|---|
| | Dry Film Conc. Parts | Wet % w/w | Dry Film Conc. Parts | Wet % w/w |
| Methocel E5 | 5.84 | 2.83 | 8.27 | 2.71 |
| Methocel E50 | 14.67 | 7.10 | 20.63 | 6.75 |
| Klucel JF | 2.64 | 1.28 | 3.49 | 1.14 |
| Maltodextrin M180 | 3.33 | 1.61 | 4.86 | 1.59 |
| Instant Starch B792 | 25.33 | 12.25 | 4.86 | 1.59 |
| Sodium phosphate dibasic | 1.19 | 0.58 | 1.52 | 0.50 |
| Sucralose | 7.92 | 3.83 | 11.07 | 3.62 |
| PEG 400 | 6.82 | 3.30 | — | — |
| Mint Flavor | 16.31 | 7.89 | 22.80 | 7.46 |
| Loperamide | 3.24 | 1.57 | 4.50 | 1.47 |
| Sorbitol | 12.62 | 6.10 | 17.90 | 5.86 |
| FD&C Green Blend 551 | 0.06 | 0.05 | 0.11 | 0.04 |
| Ethanol | — | — | — | — |
| Water | — | 51.63 | — | 67.27 |
| Overall Sum | 99.97 | 100.02 | 100.01 | 100.00 |
| Solids | | 48.37% | | 32.73% |

| | Example 5 | | Example 6 | |
|---|---|---|---|---|
| | Dry Film Conc. Parts | Wet % w/w | Dry Film Conc. Parts | Wet % w/w |
| Methocel E5 | 7.73 | 2.53 | 7.37 | 2.50 |
| Methocel E50 | 17.74 | 5.82 | 16.81 | 5.71 |
| Klucel JF | 3.27 | 1.07 | 3.27 | 1.11 |
| Maltodextrin M180 | 4.66 | 1.53 | 4.32 | 1.47 |
| IPC B792 | 4.66 | 1.53 | 4.68 | 1.59 |
| FD&C Red #40 | 0.01 | 0.00 | — | — |
| Mint Green Colorant | — | — | 0.08 | 0.03 |
| Prosweet G | 1.87 | 0.61 | 1.62 | 0.55 |
| Sucralose | 6.71 | 2.20 | 6.43 | 2.18 |
| PEG 400 | 3.73 | 1.22 | 3.73 | 1.26 |
| Omeprazole | 39.81 | 13.05 | 37.74 | 12.81 |
| Sorbitol | 3.69 | 1.21 | 3.51 | 1.19 |
| Spearmint Flavor | 6.12 | 2.01 | 5.54 | 1.88 |
| Sodium Hydroxide | — | — | 0.74 | 0.25 |
| Sodium Phosphate Dibasic | — | — | 4.16 | 1.41 |
| Water | — | 67.21 | — | 66.06 |
| Overall Sum | 100.00 | 99.99 | 100.00 | 100.00 |
| Solids | | 32.79% | | 33.94% |

| Example 7 | |
|---|---|
| | Dry Film Concentration Parts |
| Sorbitol | 11 |
| Sucrose | 11 |
| Vanilla Extract Pure | 17 |
| Parsley Seed Oil | 4 |
| Verde Green | 0.5 |
| Mint #2684 | 10 |
| Methocel E50 FG | 15 |

| Example 7 | |
|---|---|
| | Dry Film Concentration Parts |
| IPC B792 | 31.4 |
| Sucralose | 0.1 |
| Overall Sum | 100 |
| Solids | 31% |

| Example 8 | |
|---|---|
| | Dry Film Concentration Parts |
| Methocel E5 | 9.96 |
| Klucel JF | 7.12 |
| Maltodextrin | 14.31 |
| Instant Starch | 14.31 |
| Sucralose | 2.38 |
| Flavor | 27.00 |
| Loratadine | 10.00 |
| Sorbitol | 14.93 |
| Overall Sum | 100.01 |
| Solids | 40.89% |

| Example 9 | | |
|---|---|---|
| | Stock Soln. | grams |
| Base: | 21.7 | 10.020 |
| Methocel E5 | 6.9 | 0.691 |
| Methocel E50 | 3.4 | 0.341 |
| Klucel JF | 3.0 | 0.301 |
| Maltrin M180 | 4.2 | 0.421 |
| IPC B792 | 4.2 | 0.421 |
| Flavor | 100 | 3.015 |
| Saccharin | 100 | 0.217 |
| Dextromethorphan | 100 | 0.502 |
| Wet Total (including water) | | 13.754 |
| Dry Total | | 5.908 |

| Example 10 | | |
|---|---|---|
| | Dry Film Concentration Parts | Wet % w/w |
| Methocel E5 | 5.51 | 2.00 |
| Methocel E50 | 13.33 | 4.84 |
| Klucel JF | 2.38 | 0.87 |
| Maltodextrin M180 | 3.06 | 1.11 |
| IPC B792 | 3.66 | 1.33 |
| Sodium phosphate dibasic | 0.93 | 0.34 |
| Sucralose | 7.24 | 2.63 |
| PEG 400 | 6.69 | 2.43 |
| Cherry Flavor | 15.21 | 5.53 |
| Pseudoephedrine | 29.47 | 10.71 |
| Sorbitol | 11.86 | 4.31 |
| FD&C Red# 40 | 0.66 | 0.24 |

Example 10

| | Dry Film Concentration Parts | Wet % w/w |
|---|---|---|
| Ethanol | — | 10.20 |
| Water | — | 53.46 |
| Overall Sum | 100.00 | 100.00 |
| Solids | | 36.35% |

| | | Example | | | |
|---|---|---|---|---|---|
| | Stock Soln. | 11 grams | 12 grams | 13 grams | 14 grams |
| Base: | 21.7 | 9.826 | 9.852 | 9.967 | 81.676 |
| Methocel E5 | 6.9 | 0.678 | 0.680 | 0.688 | 5.636 |
| Methocel E50 | 3.4 | 0.334 | 0.335 | 0.339 | 2.777 |
| Klucel JF | 3.0 | 0.295 | 0.296 | 0.299 | 2.450 |
| Maltrin M180 | 4.2 | 0.413 | 0.414 | 0.419 | 3.430 |
| IPC B792 | 4.2 | 0.413 | 0.414 | 0.419 | 3.430 |
| Flavor | 100 | 3.019 | 3.011 | 3.031 | 29.313 |
| Saccharin | 100 | 0.201 | 0.204 | | |
| Taste Masked Dextromethorphan | 100 | 1.262 | 1.227 | 1.220 | 11.545 |
| Methocel E50 | 10 | | | | 11.661 |
| Sucralose | 25 | | | | 7.858 |
| Sorbitol | 70 | | | | 17.565 |
| FD&C Red #40 | 10 | | | | 1.121 |
| Maltrin M180 | 100 | 1.909 | | | |
| Wet Total (including water) | | 16.217 | 17.114 | 14.218 | 160.739 |
| Dry Total | | 8.523 | 6.580 | 6.414 | 74.120 |

| | | Example | | |
|---|---|---|---|---|
| | Stock Soln. | 15 grams | 16 grams | 17 grams |
| Base: | 14.5 | 8.935 | 3.314 | 6.205 |
| Methocel E50 | 9.3 | 0.831 | 0.308 | 0.577 |
| Maltrin M180 | 2.6 | 0.232 | 0.086 | 0.161 |
| IPC B792 | 2.6 | 0.232 | 0.086 | 0.161 |
| Flavor | 100 | 1.243 | 0.922 | 0.902 |
| Taste Masked Dextromethorphan | 100 | 2.453 | 1.264 | 1.239 |
| Sucralose | 25 | 0.548 | 0.280 | 0.274 |
| FD&C Red #40 | 1 | 0.507 | 0.242 | 0.238 |
| PEG 400 | 100 | 0.608 | | |
| PVP K29/32 | 55.19 | 0.908 | 2.376 | 1.664 |
| Polyethyene oxide (about 200,000 daltons) | 100 | | | |
| Wet Total | | 15.202 | 8.398 | 10.522 |
| Dry Total | | 6.243 | 4.050 | 4.030 |

| | | Example | | |
|---|---|---|---|---|
| | Stock Soln. | 18 grams | 19 grams | 20 grams |
| Base: | 20.3 | 81.930 | | |
| Methocel E5 | 6.1 | 4.998 | | |
| Methocel E50 | 4.3 | 3.523 | | |
| Klucel JF | 2.7 | 2.212 | | |
| Maltrin M180 | 3.6 | 2.949 | | |
| IPC B792 | 3.6 | 2.949 | | |
| Flavor | 100 | 25.765 | 0.995 | 1.102 |
| Taste Masked Dextromethorphan | 100 | 51.970 | 1.229 | 1.226 |
| Methocel E50 | 10 | 101.579 | | |
| Sucralose | 25 | 10.397 | 0.289 | 0.283 |
| Sorbitol | 70 | 15.388 | | |
| FD&C Red #40 | 1 | | 0.269 | 0.261 |
| FD&C Red #40 | 10 | 1.057 | | |
| PEG 400 | 100 | 12.026 | | |
| PVP | 55.19 | | 1.617 | 1.612 |
| Polyethyene oxide (about 200,000 daltons) | 100 | | 0.891 | 0.909 |
| Water | | 170.08476 | | |
| Wet Total (including water) | | 300.112 | 9.233 | 8.836 |
| Dry Total | | 130.027 | 4.082 | 4.200 |

Example 21

| | Dry film Concentration Parts |
|---|---|
| Methocel E5 | 6.14164 |
| Methocel E50 FG | 4.34101 |
| Klucel JF | 2.71067 |
| Maltrin M180 | 3.70464 |
| IPC B792 | 3.70193 |
| Sorbitol | 18.5 |
| Sucralose | 2 |
| FD&C Red #40 | 0.15 |
| Flavor | 40.0001 |
| Taste Masked Dextromethorphan | 18.75 |
| Overall Sum | 100 |
| Solids | 53% |

Example 22

| | Dry Film Concentration % w/w | Casting Solution Concentration % w/w |
|---|---|---|
| Methocel E5 | 3.96 | 1.62 |
| Methocel E50 | 6.71 | 2.75 |
| Klucel JF | 2.07 | 0.848 |
| Maltrin M180 | 5.01 | 2.05 |
| IPC B792 | 4.73 | 1.94 |
| Flavor | 0.65 | 0.266 |
| Taste Masked Diphenhydramine | 60.05 | 24.60 |
| Sucralose | 6.74 | 2.76 |
| Sorbitol | 4.40 | 1.80 |
| FD&C Red #40 | 0.11 | 0.0434 |
| PEG 400 | 5.58 | 2.29 |
| Ethanol | | 9.84 |
| Water | | 49.19 |
| Overall Sum | 100 | 100 |

Examples 21 and 22 showed disintegration times of about 0 seconds to about 12 seconds for samples of about 35 grams to about 160 grams and for film thicknesses within the range of about 20μ to about 200μ.

Disintegration times were determined using the test provided by (USP) 24, Disintegration <701>.

Example 23

| | Dry Film Concentration % w/w | Wet Parts |
|---|---|---|
| Methocel E5 | 28.50 | 6.49 |
| Methocel E50 | 13.35 | 3.04 |
| ProSweet G | 4.83 | 1.1 |
| Aspartame | 0.92 | 0.21 |
| Sucralose | 3.95 | 0.9 |
| Flavor | 11.77 | 2.68 |
| Caffeine | 36.67 | 8.35 |
| Overall Sum | 100 | 22.77 |
| Solids | 21.62% | |

Example 24

| | Dry Film Concentration Parts |
|---|---|
| Methocel E5 | 24.20 |
| Methocel E50 | 11.33 |
| ProSweet G | 4.10 |
| Aspartame | 0.78 |
| Sucralose | 3.36 |
| Flavor | 9.99 |
| Caffeine | 31.13 |
| PEG 400* | 15.10 |
| Overall Sum | 100.0001 |
| Solids | 26.56% |

*The weight % of PEG can range, for example, from between about 15% to about 52%.

Example

| | 25 | | 26 | | 27 | |
|---|---|---|---|---|---|---|
| | Dry Film Conc. Parts | Wet % w/w | Dry Film Conc. Parts | Wet % w/w | Dry Film Conc. Parts | Wet % w/w |
| Methocel E5 | 7.55 | 2.52 | 7.26 | 2.45 | — | — |
| Methocel E50 | 20.71 | 6.92 | 20.02 | 6.75 | 28.89 | 6.73 |
| Klucel JF | 3.36 | 1.12 | 3.22 | 1.08 | 3.43 | 0.80 |
| Maltodextrin M180 | 4.67 | 1.56 | 4.56 | 1.54 | 8.58 | 2.00 |
| IPC B792 | 4.58 | 1.53 | 4.43 | 1.49 | 8.54 | 1.99 |
| Sucralose | 8.92 | 2.98 | 12.48 | 4.21 | 13.80 | 3.22 |
| PEG 400 | 22.50 | 7.52 | 15.15 | 5.11 | 6.40 | 1.49 |
| Menthol | 9.81 | 3.28 | 20.42 | 6.89 | 14.53 | 3.39 |
| Sorbitol | 17.92 | 5.99 | 12.33 | 4.16 | 15.83 | 3.69 |
| $TiO_2$ | — | — | 0.15 | 0.05 | — | — |
| Ethanol | — | 3.28 | — | 6.89 | — | 3.39 |
| Water | — | 63.30 | — | 59.39 | — | 73.30 |
| Overall Sum | 100.02 | 100.00 | 100.02 | 100.01 | 100.00 | 100.00 |
| Solids | | 33.42% | | 33.72% | | 23.31% |

Example 28

| | Dry Film Concentration % w/w | Casting Solution Concentration % w/w |
|---|---|---|
| Methocel E5 | 4.51 | 1.77 |
| Methocel E50 | 8.66 | 3.41 |
| Klucel JF | 1.84 | 0.72 |
| Maltodextrin M180 | 2.85 | 1.12 |
| IPC B792 | 2.66 | 1.05 |
| Sodium phosphate dibasic | 1.62 | 0.638 |
| Sucralose | 9.59 | 3.78 |
| PEG 400 | 6.83 | 2.69 |
| Cherry Flavor | 14.47 | 5.70 |
| Pseudoephedrine | 24.39 | 9.60 |
| Sorbitol | 10.49 | 4.13 |
| FD&C Red# 40 | 0.107 | 0.0419 |
| FD&C Blue# 1 | 0.00128 | 0.000506 |
| Avicel PH105 | 11.98 | 4.72 |
| Ethanol | | 11.38 |
| Water | | 49.25 |
| Overall Sum | 100 | 100 |
| Solids | | 39.37 |

Example 29

| | Dry Film Concentration % w/w | Casting Solution Concentration % w/w |
|---|---|---|
| Methocel E5 | 2.49 | 1.05 |
| Methocel E50 | 6.93 | 2.92 |
| Klucel JF | 1.48 | 0.624 |
| Maltodextrin M180 | 2.12 | 0.891 |
| IPC B792 | 2.24 | 0.944 |
| Sucrose | 4.26 | 1.79 |
| Sucralose | 10.06 | 4.23 |
| PEG 400 | 1.55 | 0.652 |
| Crème de Menthe Flavor | 17.92 | 7.54 |
| Pseudoephedrine | 19.43 | 8.17 |
| Sorbitol | 8.32 | 3.50 |
| FD&C Red# 40 | 0.883 | 0.371 |
| FD&C Blue# 1 | 0.00166 | 0.000699 |
| Avicel CE15 | 22.31 | 9.38 |

Example 29

| | Dry Film Concentration % w/w | Casting Solution Concentration % w/w |
|---|---|---|
| Ethanol | | 21.12 |
| Water | | 36.83 |
| Overall Sum | 100 | 100 |
| Solids | | 42.06% |

Example 30

| | Dry Film Concentration % w/w |
|---|---|
| Methocel E5 | 8.09 |
| Methocel E4M | 3.66 |
| Methocel SG A16M | 4.45 |
| Plasdone K29-32 | 2.79 |
| Sucralose | 1.70 |
| Silica Gel | 4.14 |
| Pluracare F87 Prill | 20.13 |
| Avicel PH200 | 31.04 |
| Glycerin | 11.49 |
| PEG 400 | 11.28 |
| Papain | 0.408 |
| Sodium Phosphate Monobasic | 0.201 |
| Sodium Phosphate Dibasic | 0.215 |
| FD&C Blue #1 | 0.00206 |
| Cetylpyridium Chloride | 0.402 |
| Overall Sum | 100 |
| Solids | 20.11% |

Example 31

| | Dry Film Concentration % w/w |
|---|---|
| Methocel E5 | 12.06 |
| Methocel E4M | 5.41 |
| Methocel SG A16M | 6.58 |
| Sorbitol | 11.63 |
| Calcium Stearate | 10.03 |
| Sodium Saccharin | 2.01 |
| Silica Gel | 5.03 |
| SLS | 0.503 |
| Avicel PH105 | 36.68 |
| Triacetin | 9.06 |
| Papain | 0.481 |
| Sodium Phosphate Monobasic | 0.251 |
| Sodium Phosphate Dibasic | 0.257 |
| FD&C Blue #1 | 0.00254 |
| Overall Sum | 100 |
| Solids | 20% |

The formulation of example 31 was aerated prior to casting and drying. A liquid flavor was applied to the dry film such that the flavor concentration was approximately 15% w/w of the total mass of the flavored film.

Example 32

| | Dry Film Components Parts |
|---|---|
| Methocel E5 | 6.14 |
| Methocel E50 | 4.34 |
| Klucel JF | 2.71 |
| Maltrin M180 | 3.70 |
| IPC B792 | 3.70 |
| Sorbitol | 18.5 |
| Sucralose | 2.0 |
| Triclosan | 0.05 |
| Overall Sum | 41.14 |

Example 32 is directed to films with anti-microbial properties for the treatment of rashes, such as diaper rash. Various antimicrobial agents other than triclosan may be used. Such antimicrobial agents include, for example, but not limited to, Irgaguard B5000 series and B7000 series sold by Ciba Specialty Chemical.

Example 33

| | Dry Film Components Parts |
|---|---|
| Allantoin | 0.5 |
| Methocel E5 | 8.3 |
| Methocel E50 | 3.5 |
| Klucel JF | 2.1 |
| Maltrin M180 | 2.3 |
| IPC B792 | 2.3 |
| Polyethylene glycol 400 | 12.0 |
| Overall Sum | 31.0 |

Example 34

| | Dry Film Components Parts |
|---|---|
| Methocel E5 | 6.91 |
| Methocel E50 | 3.41 |
| Klucel JF | 3.01 |
| Maltrin M180 | 4.21 |
| IPC B792 | 4.21 |
| Benzocaine | 0.50 |
| Sorbitol | 5.66 |
| Overall Sum | 27.91 |

Example 35

| | Dry Film Components Parts |
|---|---|
| Methocel E5 | 6.1 |
| Methocel E50 | 4.3 |
| Klucel JF | 2.7 |
| Maltrin M180 | 3.6 |
| IPC B792 | 3.6 |
| Sucralose | 8.4 |
| Sorbitol | 12.4 |
| Polyethylene glycol 400 | 10.1 |

-continued

Example 35

| Dry Film Components | Parts |
|---|---|
| Polyvinyl pyrrolidone | 0.9 |
| Papain | 0.5 |
| Overall Sum | 52.6 |

Example 36

| Dry Film Components | Parts |
|---|---|
| Methocel E5 | 1.7 |
| Methocel E50 | 3.4 |
| Klucel JF | 0.7 |
| Maltrin M180 | 1.2 |
| IPC B792 | 1.1 |
| Sucralose | 3.8 |
| Sorbitol | 4.1 |
| Polyethylene glycol 400 | 3.8 |
| Aluminum sulfate | 0.5 |
| Overall Sum | 20.3 |

Example 37

| Dry Film Components | |
|---|---|
| Gantrez S97 | 29% |
| Gafquat HS-100 (cationic resin of PVP/methacrylamide) | 33% |
| Polyethylene glycol 400 | 38% |
| Overall Sum | 100% |

Example 33 illustrates a film composition for wound care to promotes tissue growth; example 34 illustrates a film composition for pain relief; example 35 illustrates a film composition containing an enzyme to aid in the debridement of wounds; example 36 illustrates a film composition for aiding in blood coagulation of wounds; and example 37 illustrates an example of a disintegratable film having adhesive properties.

The above description is only illustrative of preferred embodiments which achieve the objects, features and advantages of the present invention. It is not intended that the present invention be limited to the illustrated embodiments. Any modification of the present invention which comes with the spirit and scope of the following claims is considered part of the present invention.

What is claimed as new and desired to be protected by Letters Patent of the United States is:

1. A method for delivering a pharmaceutically or cosmetically active agent to a surface of a human or animal body, comprising:
    providing a dissolvable film comprising:
        a first water soluble polymer in an amount of from 2 to 35 weight percent comprising at least one hydroxypropyl methylcellulose polymer having a molecular weight of about 30,000 daltons;
        a second water soluble polymer in an amount of from 2 to 35 weight percent comprising at least one hydroxypropyl methylcellulose polymer having a molecular weight of about 90,000 daltons
        at least one pharmaceutically or cosmetically active agent;
        at least one hydroxypropyl cellulose having a molecular weight of about 140,000 daltons;
        at least one starch component;
        at least one polysaccharide component; and
        at least one of a plasticizer, humectant or a combination thereof,
        wherein the film is essentially free of surfactant, and the first and second water soluble polymers are present in relative amounts such that the film disintegrates to release the active ingredient after contact with or exposure to a moist body surface; and
    applying the dissolvable film to adhere to the body surface for a sufficient time for the film to release the active agent.

2. The method of claim 1 wherein the film is adhesive when exposed to moisture.

3. The method of claim 1 wherein the film is part of a multilayer device.

4. The method of claim 3 wherein the multilayer device comprises a structure selected from the group consisting of a bandage, wound dressing, and gauze structure.

5. The method of claim 1 wherein the film is part of a device that comprises multiple layers of dissolvable films.

6. The method of claim 5 wherein one or more of the multiple layers have different dissolution rates.

7. The method of claim 1 wherein the film further comprises polyvinyl pyrrolidone.

8. The method of claim 1 wherein a plasticizer is present and the plasticizer is selected from the group consisting of sorbitol, polyethylene glycol, and polyethylene oxide.

9. The method of claim 1 wherein the polysaccharide component comprises maltodextrin.

10. The method of claim 1 wherein the film is in a unit dosage form.

* * * * *